(12) United States Patent
Ben-Eliezer et al.

(10) Patent No.: US 10,281,544 B2
(45) Date of Patent: May 7, 2019

(54) METHOD AND DEVICE FOR ACCURATE QUANTIFICATION OF $T_2$ RELAXATION TIMES BASED ON FAST MULTI SPIN-ECHO NMR SEQUENCES

(71) Applicant: New York University, New York, NY (US)

(72) Inventors: Noam Ben-Eliezer, Bronx, NY (US); Kai Tobias Block, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 653 days.

(21) Appl. No.: 14/830,631

(22) Filed: Aug. 19, 2015

(65) Prior Publication Data

US 2015/0355298 A1     Dec. 10, 2015

Related U.S. Application Data

(63) Continuation of application No. PCT/US2014/017692, filed on Feb. 21, 2014.
(Continued)

(51) Int. Cl.
    *G01R 33/50*     (2006.01)
    *A61B 5/055*     (2006.01)
    *G01R 33/48*     (2006.01)

(52) U.S. Cl.
    CPC .............. *G01R 33/50* (2013.01); *A61B 5/055* (2013.01); *G01R 33/4824* (2013.01)

(58) Field of Classification Search
    CPC ..... A61B 5/055; G01R 33/4824; G01R 33/50; G01R 33/561; G01R 33/5615; G01R 33/4816; G01R 33/4625
    See application file for complete search history.

(56) References Cited

U.S. PATENT DOCUMENTS

| | | |
|---|---|---|
| 4,502,007 A | 2/1985 | Mee et al. |
| 2006/0164084 A1 | 7/2006 | Lomnes |

(Continued)

FOREIGN PATENT DOCUMENTS

| | | |
|---|---|---|
| RU | 2277707 | 6/2006 |
| SU | 1130784 | 12/1984 |

OTHER PUBLICATIONS

Prasloski, Thomas, et al. "Applications of stimulated echo correction to multicomponent T2 analysis." Magnetic resonance in medicine 67.6 (Oct. 2011): 1803-1814.*

(Continued)

*Primary Examiner* — Rishi R Patel
(74) *Attorney, Agent, or Firm* — Foley & Lardner LLP

(57) ABSTRACT

A method and a device are provided that improve quantification of the spin-spin relaxation ("$T_2$") time of an image in nuclear magnetic resonance ("NMR") applications using fast multi spin-echo sequences. The method employs time-efficient computer simulations for exact modeling of spurious stimulated echoes in multi-dimensional magnetic resonance imaging ("MRI") runs. The method employs Bloch simulations and can use a plurality of parameters to produce echo modulation curves prior to correcting distorted experimental data based on pre-calculated simulation values.

24 Claims, 9 Drawing Sheets

Related U.S. Application Data

(60) Provisional application No. 61/767,663, filed on Feb. 21, 2013.

(56) References Cited

U.S. PATENT DOCUMENTS

| | | | | |
|---|---|---|---|---|
| 2012/0268123 A1* | 10/2012 | Griswold | ............ | G01R 33/448 324/309 |
| 2015/0006114 A1* | 1/2015 | Altbach | ................ | A61B 5/055 702/189 |

OTHER PUBLICATIONS

International Search Report and Written Opinion for Application No. PCT/US2014/017692, dated May 29, 2014, 6 pages.

\* cited by examiner

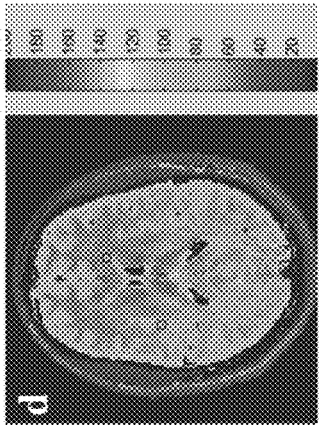
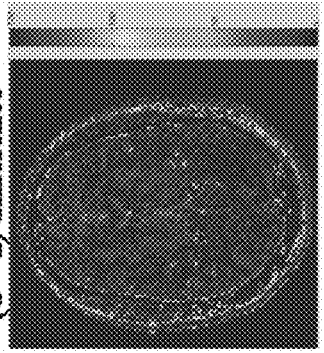
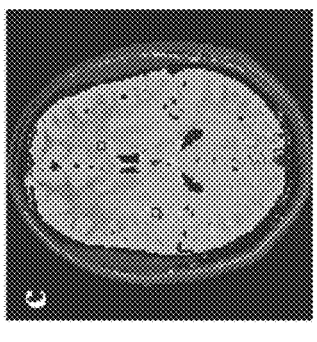
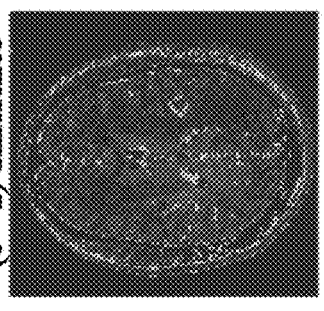
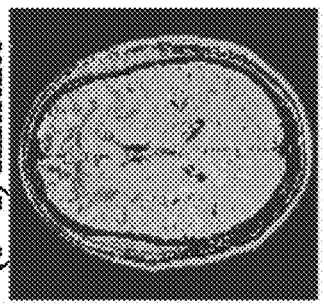
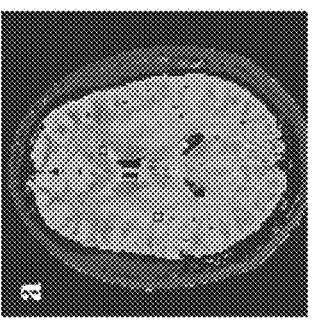
FIG. 3(d)
FIG. 3(c)
FIG. 3(b)
FIG. 3(a)

| Protocol / reconstruction | Ordering | T2 [ms] | T2 [ms] |
|---|---|---|---|
| Single-Echo Spin-Echo | Cartesian | 88 | 45 |
| RAISE (conventional exponential fit) | Radial | 111 | 63 |
| RAISE (model based fit) | | 86 | 40 |

METHOD AND DEVICE FOR ACCURATE QUANTIFICATION OF $T_2$ RELAXATION TIMES BASED ON FAST MULTI SPIN-ECHO NMR SEQUENCES

CROSS REFERENCE TO RELATED APPLICATIONS

This application is a Continuation of International Application PCT/US2014/017692 filed on Feb. 21, 2014, which claims priority from U.S. Provisional Application No. 61/767,663 filed Feb. 21, 2013, both of which are hereby incorporated by reference in their entireties.

FIELD OF THE INVENTION

The present invention relates generally to the field of quantification of spin-spin relaxation time ("$T_2$") assessment for diagnosis and prognosis. Specifically, the present invention relates to methods and devices for accurately quantifying $T_2$ relaxation times based on fast multi spin-echo nuclear magnetic resonance ("NMR") sequences.

BACKGROUND $T_2$ contrast is one of the most commonly used tools for non-invasive diagnosis and prognosis of pathologies. Although $T_2$ assessment is usually done in a visually qualitative manner, its quantitative characterization holds valuable information for numerous applications. These applications include the detection of biochemical and biophysical changes in hip and knee cartilage, diagnosis of prostate and liver cancer, assessment of diseased and post-transplant myocardial edema, the investigation of muscle physiology, for example, as well as many other applications.

Problems exist with the current methods of quantifying $T_2$ relaxation times. Genuine quantification of $T_2$ remains highly challenging in clinical practice due to long scan times associated with full single-echo spin-echo ("SE") acquisitions, which can be on the order of dozens of minutes.

Quantification of true underlying $T_2$ relaxation times is rendered difficult for fast multi spin-echo sequences ("MSE") due to an inherent bias of the calculated $T_2$ values resulting from contamination of a train of echoes by stimulated and indirect echoes, as shown in FIG. 1a. The difficulty is exacerbated because a train of spin-echoes, sampled at intervals of $\Delta t$, will not obey a theoretical exponential decay as shown in Equation 1:

$$\text{Signal}(t=n\cdot\Delta t)=\text{Signal}(0)\times e^{-(n\cdot\Delta t)/T_2} \quad n=0,1,2\ldots,N \quad \text{(Eq. 1)}$$

Instead, the train will be distorted by the accumulated effect of recurring echoes that originate from earlier parts of the echo train.

Further complications ensue because most fast quantification methods are additionally sensitive to main ("$B_0$") and transmit ("$B_1$") field inhomogeneities, non-rectangular slice profiles, and diffusion weighting. Several approaches have recently been proposed for overcoming such artifacts using either analytical or numerical stepwise tracing of all coherence pathways arising in a multi-echo sequence. Some of these methods appear to show promising preliminary results. However, these approaches suffer from at least one of the following limiting aspects: they entail high numerical complexity, do not allow straightforward deduction of a $T_2$ value from an experimentally measured train of echoes, fail to account for $T_1$ or $T_2$ relaxation during the radio-frequency ("RF") pulse application, and generally do not account for all relevant experimental factors.

A need exists for improved technology, including technology that may address the above described disadvantages.

SUMMARY OF THE INVENTION

Embodiments of the present invention provide methods for generating $T_2$-maps in clinically feasible scan times using general MSE sequence designs (i.e., sequence design that implement a train of spin-echo acquisitions following a single excitation radiofrequency pulse) based on using Bloch simulations of the experimental pulse sequence. Such Bloch simulations are not necessarily full-scale Bloch simulations, which can be infeasible because they require extremely high numerical complexity. The requisite numerical complexity can be reduced if proper simulation assumptions are relied upon that preserve the simulation's fidelity to the actual experimentation. Such methods enable accurate modeling of all coherence pathways and further permit the incorporation of a plurality of experimental factors such as radio frequency ("RF") pulse shapes, spin diffusion, $B_0$ and $B_1$ non-uniformities, and the presence of multiple $T_2$ components.

Embodiments of the present invention provide methods employing time-efficient one-dimensional computer simulations for exact modeling of spurious stimulated echoes in multi-dimensional magnetic resonance imaging ("MRI") experiments, followed by the use of pre-calculated simulation data to correct distorted experimental data.

Certain embodiments of the present invention encompass devices that are designed to implement the aforementioned methods according to the invention.

Additional features, advantages, and embodiments of the present disclosure may be set forth from consideration of the following detailed description, figures, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE FIGURES

The accompanying figures, which are included to provide further understanding of the invention, are incorporated in and constitute a part of this specification, illustrate the advantageous results produced by embodiments of the present disclosure and, together with the detailed description, serve to explain the principles of the present disclosure. No attempt is made to show details of the present disclosure to a greater extent than may be necessary for a fundamental understanding of the present disclosure and the various ways in which it may be practiced.

FIG. 3(a) illustrates a $T_2$ map for an in vivo human brain generated using a gold-standard conventional $T_2$ measurement based on a time-inefficient single spin-echo protocol.

FIG. 3(b) illustrates a $T_2$ map for an in vivo human brain generated using a fast multi spin-echo (MSE) protocol produced by a conventional fit to an exponential decay curve following Eq. 1.

FIG. 3(c) illustrates a $T_2$ map for an in vivo human brain generated using a fast multi spin-echo protocol but fitted using simulated echo modulation curves according to an embodiment of the present invention.

FIG. 3(d) illustrates a $T_2$ map for an in vivo human brain generated using a fast multi spin-echo protocol fitted using simulated echo modulation curves according to an embodiment of the present invention that further incorporates additional fitting to a radiofrequency ("RF") scaling factor denoted by $B_1$, thereby providing for a joint $T_2$ and $B_1$ fitting procedure.

DETAILED DESCRIPTION OF PREFERRED EMBODIMENTS

Figure 1A:
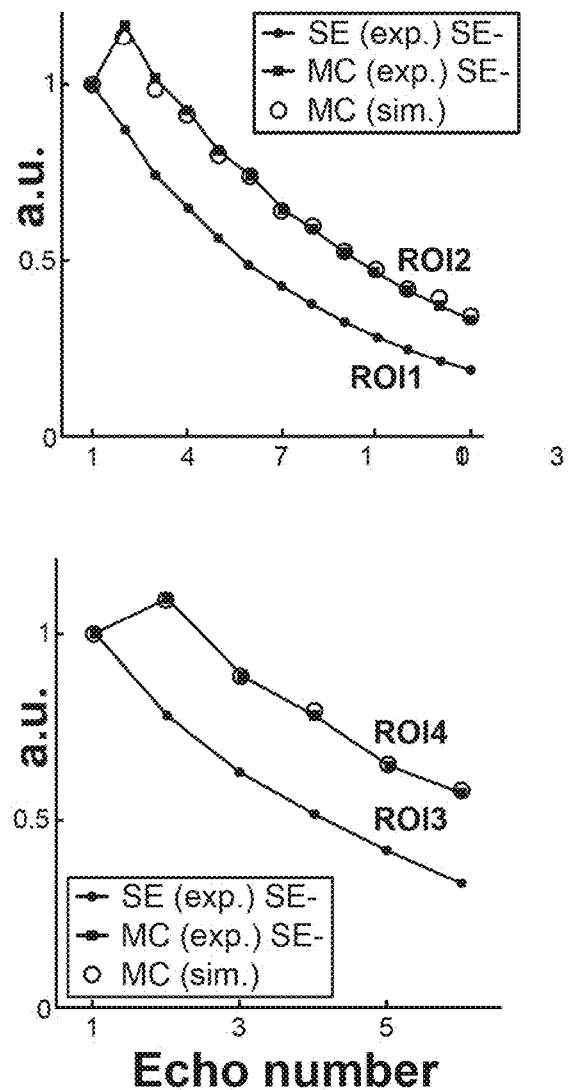
FIG. 1(a) illustrates experimental echo modulation decay curves for SE and MSE and corresponding simulation values from Bloch simulations.

In the following detailed description, reference is made to the accompanying figures, which form a part hereof. In the figures, similar symbols typically identify similar elements, unless context dictates otherwise. The illustrative embodiments described in the detailed description, figures, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be performed, arranged, substituted, combined, and designed in a wide variety of different configurations, all of which are explicitly contemplated and made part of this disclosure.

In some embodiments of the present invention, a preparation stage exists with a duration on the order of minutes to hours. In some embodiments, the preparation stage includes Bloch simulation of the prospective MSE pulse sequence, performed on a standard personal computer ("PC") or a faster dedicated machine. In some embodiments, the Bloch simulation uses a plurality of parameters. One parameter of the plurality of parameters can be an exact RF pulse shape based on amplitude and phase. Another parameter of the plurality of parameters can be an echo train length ("ETL") value. Others of the plurality of parameters include additional experimental parameters including, but not limited to: a spatial distribution of the $B_1$ transmit field, a spatial distribution of the main $B_0$ magnetic field, a frequency off-resonance of the main $B_0$ magnetic field, a spatial distribution of the $T_1$ relaxation time, a spatial distribution of a diffusion coefficient, a slice thickness, an acquisition bandwidth, an acquisition duration, and magnetic field gradient events that are applied during the pulse sequence. Although the Bloch simulations of some embodiments of the present invention include the plurality of parameters, other embodiments include Bloch simulations that may use only a subset of the plurality of parameters.

In some embodiments of the present invention, the Bloch simulation uses a first sequence that is a conventional multi-echo protocol. The protocol of these embodiments employs a Cartesian k-space sampling scheme in which following a single spin-excitation event each echo train scans the same line for a number of times in accordance with the ETL value, corresponding respectively to increasing echo times ("TEs"). This procedure yields a data set that can be rearranged to produce a set of ETL images, each having a different $T_2$ weighting (e.g., 1×TE, 2×TE, . . . , ETL×TE).

In some embodiments of the present invention, the Bloch simulation uses a second sequence that is a multi-echo protocol based on radial sampling of the k-space. In these embodiments, the protocol scans each radial spoke only once. Furthermore, the protocol uses a unique spoke ordering scheme that can be advantageous in some applications, including at least one embodiment of the present invention. For example, the spoke ordering scheme maximizes the difference between each spoke, where the difference of the angles of the spokes should be as close to 90° as possible. Such maximization distributes spokes evenly around the k-space and minimizes any time-local motion artifacts. It follows that in such embodiments, the protocol avoids focusing on specific k-values and minimizes the $T_2$ weighting difference between adjacent k-space lines in order to produce a smoothly changing k-space sampling pattern. Another example is the use of golden-angle increments between each consecutive spokes.

In some embodiments of the present invention, a plurality of Bloch simulations are run for a range of a chosen subset of the plurality parameters, e.g., $T_2$ and $B_1$ parameter values. The plurality of Bloch simulations are run irrespective of whether the first sequence or the second sequence is used. The plurality of Bloch simulations can be repeated for a practical range of $T_2$ values expected in the experiment (e.g., $T_2=1 \ldots 500$ ms in increments of $\Delta T_2=1$ ms). The plurality of Bloch simulations can be repeated for a range of RF transmit ($B_1$) field scaling values expected in the experiment (e.g., $B_1=40\% \ldots 110\%$ in increments of $\Delta B_1=1\%$). The plurality of Bloch simulations can be repeated for a practical range of $T_1$ values expected in the experiment (e.g., $T_1=100 \ldots 5000$ ms in increments of $\Delta T_1=100$ ms). The plurality of Bloch simulations can be repeated for a practical range of $\Delta B_0$ values expected in the experiment (e.g., $\Delta B_0=10 \ldots 1000$ Hz in increments of $\Delta B_0=00$ Hz). In at least one embodiment of the invention, such repetition subsequently produces a set of echo modulation curves, each associated with a distinct $T_2$ value and a distinct $B_1$ value.

In at least one embodiment, Bloch simulations can be repeated for a practical range of $T_2$ values expected in the experiment (e.g., $T_2=1 \ldots 500$ ms in jumps of $\Delta T_2=1$ ms). Each of such simulation runs yields a set of echo modulation curves ("EMCs"), and each curve is associated with a unique $T_2$ value. The repetition of the simulations across such a range of produces data that may be stored in a database and used for analysis, validation, and other purposes. Such a database can include EMCs for ranges of both $T_2$ values and transmit field scales, allowing identification of a $T_2$ value with an EMC that most closely corresponds to experimentally measured data at a given voxel.

The method of at least one embodiment can be incorporated into computer software or implemented using commercial analytical simulation software, standard statistical packages, or a plurality of programming environments.

Figures 1B, 1C, 1D:
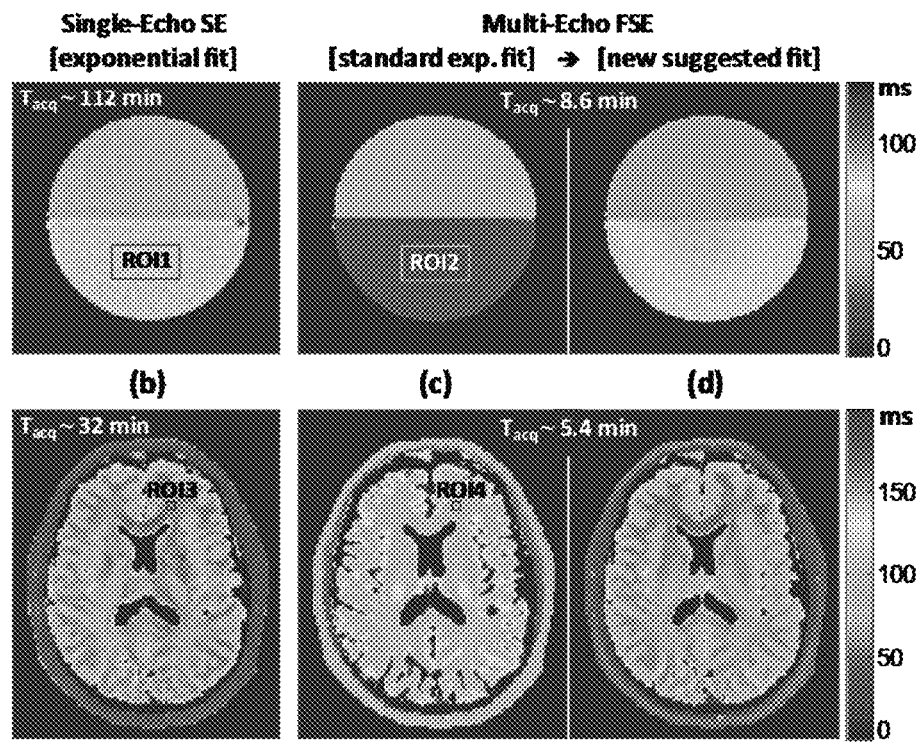
FIG. 1(b) illustrates $T_2$ maps generated from a gold-standard SE sequence data set, with conventional data fitting, i.e., fitting to a conventional exponential decay as seen in Eq. 1.
FIG. 1(c) illustrates MSE based $T_2$ maps using an exponential fit similar to the conventional data fitting of FIG. 1(b).
FIG. 1(d) illustrates MSE based $T_2$ maps generated from the same data set used in FIG. 1(c), but fitted—using a best Euclidean error norm (the "$L_2$ norm") or a piecewise linear correlation test—to a pre-calculated echo modulation curve that is generated by simulating the MSE pulse-sequence according to an embodiment of the present invention.

In at least one embodiment, a standard MSE protocol is employed to acquire data on any MRI scanner available on any existing commercial scanner. As shown in FIG. 1, one embodiment of the present invention utilized data acquired on a 3T whole-body Siemens scanner. FIGS. 1(a)-1(d) depict results for a two-compartment phantom and an in vivo human brain. As shown in FIGS. 1(b)-1(d), a full gold-standard SE protocol can be compared to a multi-echo MSE protocol that employs identical experimental parameters. In at least one embodiment, data acquisition is performed in order to produce a set of echo modulated curves based on experimental data.

In at least one embodiment, data can be acquired on any MRI scanner using either a standard multi spin-echo protocol available on commercial scanners or using a customized multi spin-echo protocol as described above. In at least one embodiment, the customized multi spin-echo protocol is a non-standard radial protocol.

In at least one embodiment, post-processing occurs on the order of seconds to minutes per two-dimensional slice. During post-processing, at least one $T_2$ map is generated by fitting MSE data to a set of echo modulation curves which were pre-calculated during runs of the Bloch simulation. In one embodiment, a $T_2$ map can be generated by fitting MSE data to a set of echo modulation curves which were pre-calculated during a single run of the Bloch simulation. In at least one embodiment, the experimental set of echo modulation curves is generated after the simulated set of echo modulation curves have been produced. In some embodiments, data is interpolated from at least one run of the simulation to enhance resolution of the $T_2$ values.

In at least one embodiment, actual fitting is dependent on the pulse-sequence scheme being used. Fitting in some embodiments is performed based on the experimental set of echo modulation curves and the simulated set of echo modulation curves. In some embodiments, fitting is performed by reducing an error norm corresponding to a difference between the experimental set of echo modulation curves and the simulated set of echo modulation curves. Comparison of the experimental and simulated sets of echo modulation curves can indicate whether such a difference is present. In some embodiments, fitting is performed by maximizing a piecewise linear correlation between the experimental set of echo modulation curves and the simulated set of echo modulation curves. In some embodiments, fitting is performed by increasing the piecewise linear correlation between the experimental set of echo modulation curves and the simulated set of echo modulation curves such that the correlation attains an effective peak value. The piecewise linear correlation in at least one embodiment exceeds a threshold value that may be predetermined.

In some embodiments, an error norm is a Euclidean norm ("$L_2$ norm"). In at least one embodiment, an error norm is reduced in accordance with a predetermined threshold. A predetermined threshold may be a discrete value in at least one embodiment. In some embodiments, a predetermined threshold may be expressed as a range of values or in relation to a distribution of values. Some embodiments may include a predetermined threshold that is expressible as a percentage. The error norm is reduced in some embodiments such that the error norm does not exceed the predetermined threshold. In some embodiments, error is less than or equal to the predetermined threshold. The predetermined threshold in some embodiments correlates to an acceptable error rate.

In some embodiments, a simple looping over all echo modulation curves is used to reduce the error norm. In at least one embodiment, error reduction is achieved using an iterative least-square optimization approach. In some embodiments, an error norm may be reduced such that the error is effectively lowered to a minimal value.

In some embodiments using the conventional multi-echo protocol, fitting is performed by reduction of the error norm based on the difference between experimental and simulated set of echo modulation curves. In some embodiments using the conventional multi-echo protocol, fitting is performed using a fitting procedure that may vary between a simple looping over all curves, an iterative least-square optimization approach, or faster search methods based on conjugate gradient algorithms.

In some embodiments, fitting is performed such that two or more quantitative parametric maps may be output. In some embodiments, two such quantitative parametric maps are a $T_2$ relaxation map and a transmit $B_1$ map. Subsequently to the outputting of the maps, the $T_2$ map is back-projected in time (to t=0 milliseconds) to produce an additional map of the proton density, before any occurrence of relaxation. The proton density map signifies the underlying water content in the tissue.

In some embodiments using the multi-echo protocol based on radial sampling of the k-space, fitting is performed as part of a global model-based reconstruction procedure employing a non-linear conjugate-gradient iterative algorithm. In some embodiments, the model based reconstruction outputs three or more quantitative parametric maps including a $T_2$ relaxation map, transmit $B_1$ map, and a Proton Density map. Use of the pre-calculated echo modulation curves in this procedure requires the integration of a non-analytic model into an analytic model and is important for realizing the advantageous effects of the present invention. The analytic model into which the non-analytical model is integrated is described in K. T. Block, M. Uecker, and J. Frahm, *Model-based iterative reconstruction for radial fast spin-echo MRI*, 28(11) IEEE TRANS MED IMAGING 1759, 1759-69 (2009), which is incorporated herein by reference in its entirety.

At least one embodiment is a device for quantifying a spin-spin relaxation time ($T_2$) including a magnetic resonance data acquisition unit and a control unit configured to generate at least one run of a simulation of a prospective fast multi spin echo (MSE) pulse sequence using at least one of a plurality of parameters to produce a first set of echo modulation curves. In at least one embodiment, the magnetic resonance data acquisition unit is coupled to the control unit, and the control unit is configured to analyze data elicited from the magnetic resonance data acquisition unit. In some embodiments, the control unit analyzes data elicited from the magnetic resonance data acquisition unit to generate a second set of echo modulation curves, permitting comparison to the first set of echo modulation curves. The second set of echo modulation curves is based on experimentally-generated data.

Some embodiments are devices including a magnetic resonance data acquisition unit and a control unit integrated into a standalone system. In other devices, each of the magnetic resonance data acquisition and the control unit may be connected for operation and utilization in conjunction with a plurality of apparatuses. Such apparatuses can include computers, diagnostic equipment, power sources, and monitors. In some embodiments, the magnetic resonance data acquisition and the control unit may provide information to at least one apparatus that is not physically connected to either the magnetic resonance data acquisition unit or the control unit. In at least one embodiment, the control unit receives or transmits information wirelessly. In some embodiments, the control unit may be a handheld device or may be operably connected to a handheld device.

As shown in FIGS. 1(a)-1(d), data comprising $T_2$ maps can be processed using a standard fit, for example, the exponential decay model of Eq. 1. Alternatively, such data can be fitted using the alternative methods of some embodiments described herein. Data fitted using such methods can be compared against data fitted using the exponential decay model. Fitted data can be compared against $T_2$ maps that have been generated using a conventional accepted gold-standard exponential fit for a set of single-echo SE images, where the exponential fit represents a conventional standard.

FIGS. 1(a)-1(d) each contain an upper portion and a lower portion. Depictions in the upper portion of each of FIGS. 1(a)-1(d) were generated based on phantom data. Depictions in the lower portion of each of FIGS. 1(a)-1(d) were generated based on brain data. Parameters for the phantom data are as follows: repetition time ("TR")=4 seconds, echo times ("TE")=[12 ... 156] ms in steps of 12 ms, number of echo times=13, echo train length=1 for SE and =13 for MSE, spatial-resolution=1.25×1.25×3 mm³, slice thickness=3 mm, acquisition time ("$T_{acquisition}$")=112 minutes for SE and =8.6 minutes for MSE. Parameters for the brain data are as follows: TR=3 seconds, TE=[20 ... 120] ms in steps of 20 ms, number of echo times=6, echo train length=1 for SE and =6 for MSE, spatial-resolution=1.7×1.7×3 mm³, slice thickness=3 mm, $T_{acquisition}$=32 minutes for SE and =5.4 minutes for MSE.

As shown in FIGS. 1(c)-1(d), a plurality of $T_2$ maps may be generated using the methods of some embodiments. FIG. 1(a) depicts experimental echo-modulation decay curves for SE sequence data and experimental and simulated decay curves for MSE sequence data. These experimental echo-modulation decay curves correspond to the second set of echo modulation curves in some embodiments, whereas the first set of echo modulation curves is based on simulated decay curves. The SE sequence data is shown on the lower curve of FIG. 1(a), i.e., the curve closest to the abscissa. The MSE data is shown on the upper curve of FIG. 1(a), i.e., the curve farther from the abscissa. SE sequence data in FIG. 1(a) corresponds to a panel shown in FIG. 1(b). FIG. 1(b) depicts $T_2$ maps generated using conventionally accepted gold-standard SE sequence data. MSE sequence data shown in FIG. 1(a) corresponds to a panel shown in FIG. 1(c).

FIGS. 1(a)-1(c) illustrate the substantial effects of stimulated echoes in multi-echo protocols. The Bloch simulations of some embodiments can predict such effects with high accuracy. Rounded dots positioned along the curves shown in FIG. 1(a) correspond to discrete data points produced by Bloch simulations.

As noted above, $T_2$ maps can be generated using conventional SE sequence data, as shown in FIG. 1(b). In some embodiments, the method includes a best-fit $L_2$ norm to fit data. The method of at least one embodiment uses a piecewise linear correlation test to fit data. FIG. 1(c) depicts MSE-based $T_2$ maps using exponential fits similar to the conventional exponential fit. FIG. 1(d) depicts the same data shown in FIG. 1(c) when a best-fit $L_2$ norm is applied to the pre-calculated set of echo-modulation-curves. FIG. 1(d) depicts results based on the methods of some embodiments. Achievement of a consistent improvement in $T_2$ accuracy using the method of some embodiments is readily visible in comparing FIGS. 1(c) and 1(d) against the conventionally-produced gold-standard $T_2$ maps in FIG. 1(a).

An embodiment used to generate results shown in FIG. 1(d) yielded marked error reduction in contrast to the standard exponential fit employed in FIG. 1(c). For the phantom data shown in the upper portion of FIGS. 1(c) and 1(d), the method of at least one of the embodiments reduced an error rate from 32% to 6% in comparison to the conventional exponential fit. For the brain data on the lower portion of FIGS. 1(c) and 1(d), such a method reduced the error rate from 70% to 17% in comparison to the conventional exponential fit.

Figure 1E:
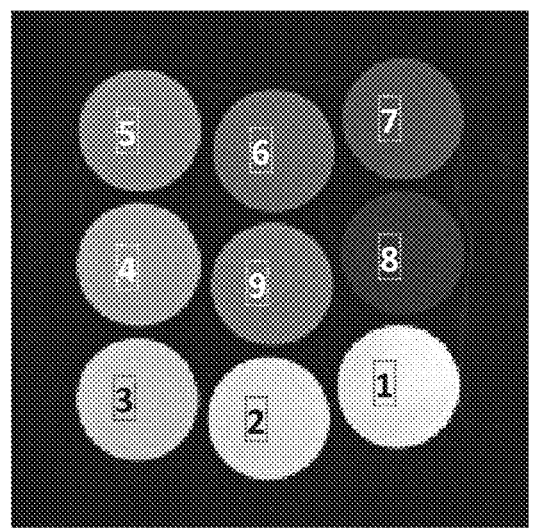
FIG. 1(e) illustrates a $T_2$ weighted fast spin echo image of a phantom.

An embodiment used to generate results shown in FIG. 1(e) produced a $T_2$ weighted fast spin echo image of a nine-tube manganese chloride ($MnCl_2$) phantom. FIG. 1(e) depicts circular tubes, numbered 1-9, which were doped with varying concentrations of $MnCl_2$. The doping imparted each tube with a different $T_2$ relaxation time. Tubes #9 and #5 were prepared with similar concentrations in order to verify $T_2$ mapping consistency over different spatial locations. Table 1 below includes representative data corresponding to FIG. 1(e).

TABLE 1

| | | $MnCl_2$ concentrations and corresponding $T_2$ values | | | | | | |
|---|---|---|---|---|---|---|---|---|
| | | Single-Echo SE [exponential fit] | Multi-Echo SE [exponential fit] | | | Multi-Echo SE [EMC fit] | | |
| | | | α Refocus → | | | | | |
| Tube # | MnCl2 [mM] ↓ | 180° | 180° | 150° | 120° | 180° | 150° | 120° |
| [1] | 0.070 | 115.9 | 155.8 | 160.6 | 177.0 | 113.9 | 113.1 | 110.7 |
| [2] | 0.135 | 67.1 | 90.7 | 93.9 | 103.9 | 64.8 | 63.8 | 62.3 |
| [3] | 0.270 | 36.7 | 50.9 | 53.4 | 60.0 | 34.7 | 34.1 | 33.4 |
| [4] | 0.405 | 23.6 | 33.9 | 35.1 | 39.2 | 22.3 | 22.1 | 21.2 |

TABLE 1-continued

MnCl$_2$ concentrations and corresponding T$_2$ values

| Tube # | MnCl2 [mM] ↓ | Single-Echo SE [exponential fit] 180° | Multi-Echo SE [exponential fit] α Refocus → | | | Multi-Echo SE [EMC fit] | | |
|---|---|---|---|---|---|---|---|---|
| | | 180° | 180° | 150° | 120° | 180° | 150° | 120° |
| [5] | 0.540 | 17.8 | 25.4 | 27.6 | 34.2 | 17.0 | 16.7 | 16.0 |
| [6] | 0.675 | 14.7 | 20.8 | 29.9 | 27.0 | 13.3 | 13.4 | 13.1 |
| [7] | 0.800 | 11.9 | 20.1 | 22.7 | 29.2 | 11.2 | 10.7 | 10.1 |
| [8] | 1.000 | 10.7 | 16.5 | 17.3 | 20.3 | 8.9 | 8.1 | 8.1 |
| [9] | 0.540 | 17.7 | 25.5 | 26.2 | 30.8 | 17.0 | 16.9 | 16.4 |
| | Average error [%] | | 44.8 | 59.1 | 80.2 | 6.3 | 8.3 | 11.0 |

Table 1 contains data for MnCl$_2$ concentrations and corresponding T$_2$ values for the phantom depicted in FIG. 1(e) and described above. T$_2$ values were obtained from either a gold-standard single SE protocol or a fast multi-SE pulse-sequence for three different refocusing flip-angles. Data was post-processed using either an exponential fit or an echo-modulation curve algorithm such as the algorithms described above. Averages of the relative errors for each T$_2$ value examined are shown in the bottom row of Table 1. The average values were calculated as the absolute difference between the single-SE and multi-SE values, divided by reference values which were single-SE reference values.

Figure 2:
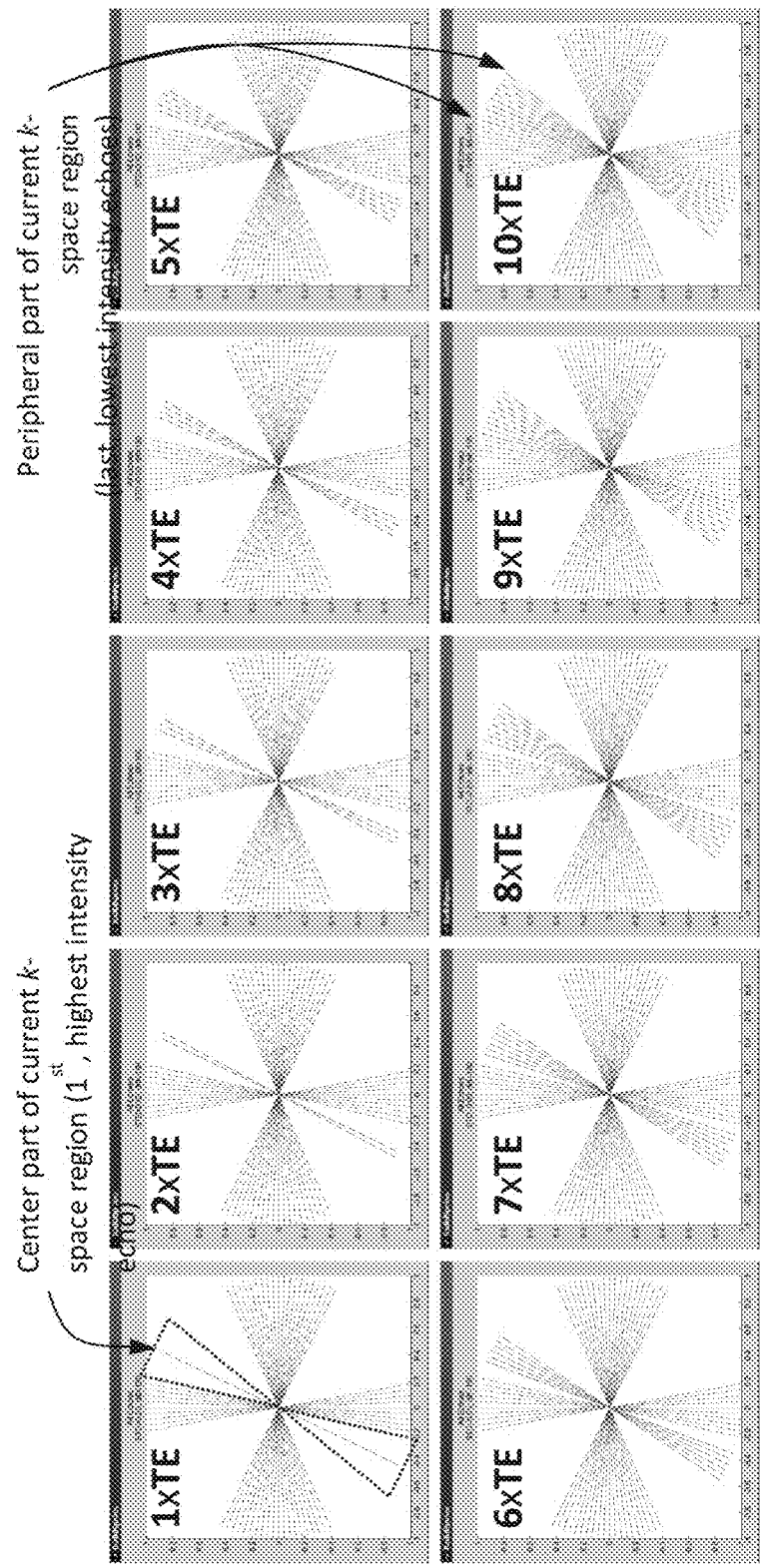
FIG. 2 illustrates an ordering mode progression within a single echo train according to an embodiment of the present invention.

FIG. 2 depicts an example of an ordering mode progression within a single echo train. In the example shown in FIG. 2, an ordering mode of radial spokes along a single echo train is shown. For FIG. 2, the parameters used are as follows: echo train length=10, number of excitations=7. The single echo train shown in FIG. 2 corresponds to a specific localized region in k-space, marked by the dotted triangles shown on the first panel. The sampling pattern of each echo train is ordered so that the first echo is positioned at the center of the specific localized region.

In the ordering mode progression shown in FIG. 2, the first echo spoke is labeled "1×TE" and has the lowest T$_2$ decay, and accordingly has the highest intensity. The sampling pattern is further ordered such that the last echo spokes cover the edges of that region. These last echo spokes are labeled "9×TE," and "10×TE," respectively, and have the strongest T$_2$ decay, corresponding to the lowest intensity. This exemplary ordering scheme produces a smooth transition of signal intensities in a final, subsequent data set. In addition, the sets of echo-trains themselves (i.e., excitations) are also ordered in such a way that angular difference between each set can be maximized so as to spread out any spurious time-dependent motion artifacts in a homogeneous way across the k-space.

FIGS. 3(a)-3(d) provides a comparison of results produced using the conventional T$_2$ measurements based on a time inefficient gold-standard single spin-echo protocol in against results from the multi spin-echo protocol. Results from the conventional T$_2$ measurements are shown in FIG. 3(a). FIGS. 3(b)-3(d) provide results for the multi spin-echo protocol of some embodiments. FIG. 3(b) depicts a map of inaccurate T$_2$ values, produced by conventional data fitting to an exponential decay curve (e.g., exp (−t/T$_2$)). FIG. 3(c) demonstrates the higher accuracy that can be achieved by fitting according to embodiments of the method of the present invention that employ simulated echo-modulation-curves.

FIG. 3(d) shows the improvement that can be gained by incorporating an RF scaling factor denoted by B$_1$ into embodiments of the method, and by using a joint T$_2$ and B$_1$ fitting procedure. The lower portions of FIGS. 3(b)-3(d) show the differences between values from the multi spin-echo protocol and the conventional values in FIG. 3(a). For FIGS. 3(a)-3(d), the parameters used are as follows: TR=2.5 seconds, TE=[15,30,45,60,75,90] ms, number of echo times=6, echo train length=1 for FIG. 3(a) and =6 for FIGS. 3(b)-3(d), spatial-resolution=1.7×1.7×3 mm$^3$, slice thickness=3 mm, T$_{acquisition}$=32:24 minutes for the SE protocol in FIG. 3(a) and T$_{acquisition}$=3:14 minutes for the multi SE protocol in FIGS. 3(b)-3(d).

Figure 4:
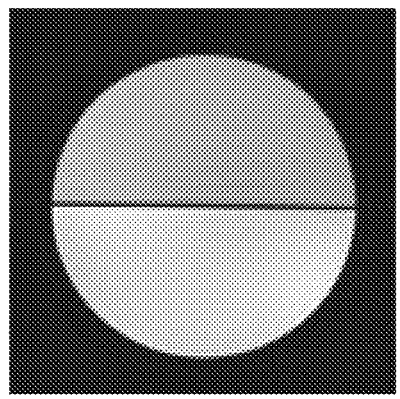
FIG. 4 illustrates proton density ("PD") and $T_2$ maps for a two compartment phantom generated, in contrast to the previous figures, using a radial, rather than a Cartesian sampling scheme for a fast multi spin-echo protocol according to an exemplary embodiment of the present invention.
Figure 4:
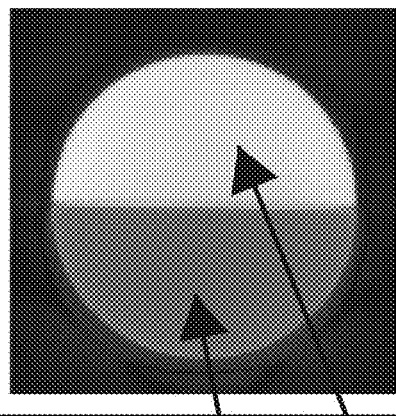

FIG. 4 depicts proton density ("PD") maps for a two compartment phantom, generated using a protocol employing a fast train of radial multi spin-echo sampling scheme. The right portion of FIG. 4 depicts R$_2$ (i.e., 1/T$_2$) data. FIG. 4 includes a table showing values from a Cartesian gold-standard single-echo spin-echo measurement [T$_2$=88 ms and 45 ms]; the values obtained by the radial sampling scheme using conventional fit to an exponential decay curve (exp(−t/T$_2$) [T$_2$=111 ms and 63 ms] and the values achieved by fitting to embodiments of the method of the present invention including simulated echo-modulation-curves [T$_2$=86 ms and 40 ms]. Parameters for FIG. 4 are as follows: TR=3 seconds, TE=[13 . . . 169] ms in steps of 13 ms, number of echo times=13, echo-train-length=13, spatial-resolution=1.3×1.3×3 mm$^3$, slice-thickness=3 mm, T$_{acquisition}$=3:00 minutes.

Figures 5A, 5B, 5C:
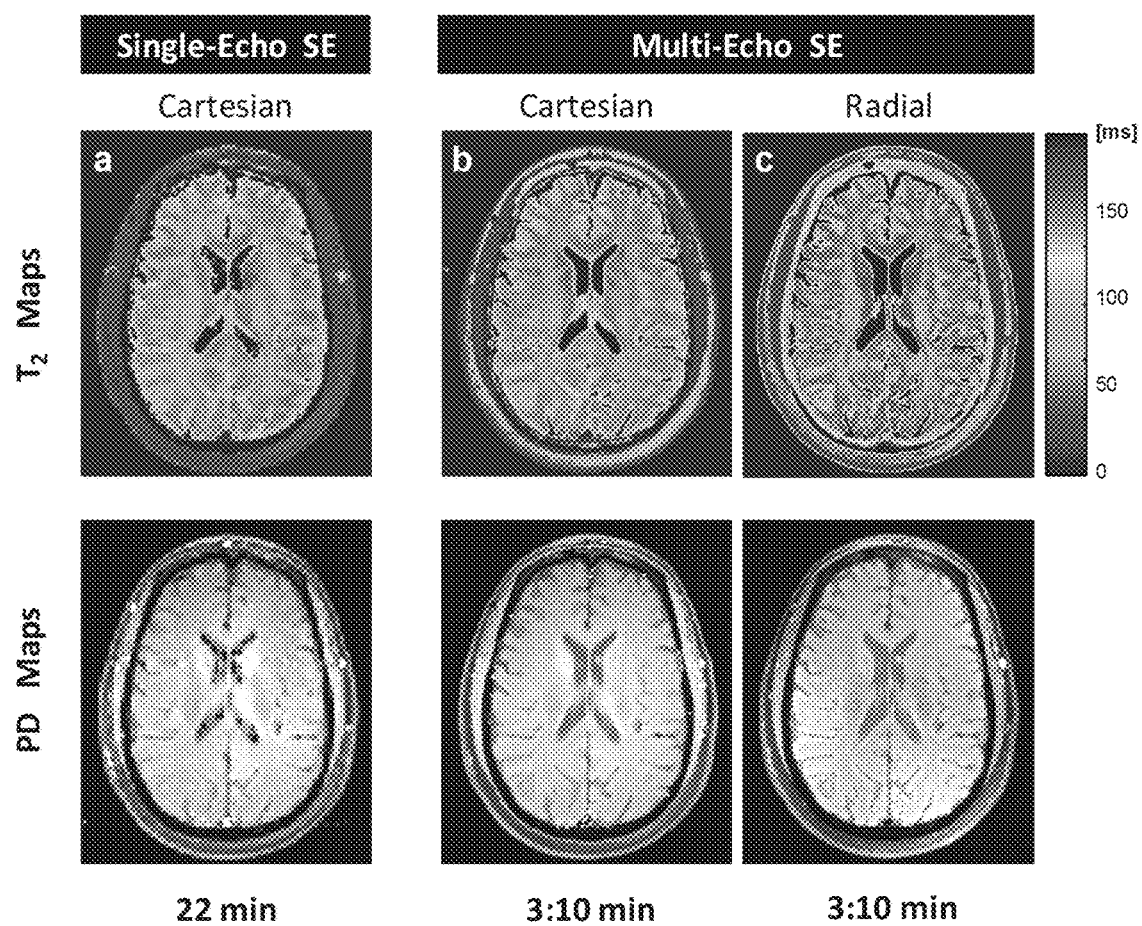
FIG. 5(a) illustrates an example $T_2$ map for an in vivo human brain generated using a conventional Cartesian sampling using a gold-standard time-inefficient single spin-echo protocol.
FIG. 5(b) illustrates a first $T_2$ map for an in vivo human brain generated using a fast multi spin-echo (MSE) protocol using a Cartesian sampling scheme and fitted to an exponential decay curve following Eq. 1.
FIG. 5(c) illustrates a second $T_2$ map for an in vivo human brain generated using a fast multi spin-echo (MSE) protocol using a Cartesian sampling scheme but fitted using simulated echo modulation curves according to an embodiment of the present invention.

FIGS. 5(a)-5(c) depict T$_2$ maps for an in vivo human brain generated using a conventional "gold-standard" T$_2$-measurement based on a time-inefficient single spin-echo protocol (shown in the top portion of FIG. 5(a)), a Cartesian multi spin-echo protocol, as shown in the top portion of FIG. 5(b), and a radial multi spin-echo protocol, shown in the top portion of FIG. 5(c). FIGS. 5(c) and 5(d) demonstrate the higher accuracy and enhanced spatial resolution that can be attained by fitting in accordance with embodiments of the method of the present invention that employ simulated echo modulation curves at least with respect to Cartesian and radially sampled data. The lower portions of FIGS. 5(a)-5(c) illustrate the underlying proton density maps that can be produced by the fitting approaches of certain embodiments, which involve joint fitting of the parameters T2, B1, and PD.

Deviations between FIGS. 5(b)-5(c) and 5(a) can be attributed to inter-scan position changes and different motion artifacts, among other things. In some cases, deviation can further be attributed to image misregistration, owing to the fact that the data may originate from different k-space sampling schemes. Parameters for FIG. 5(a) are as follows: TR=2 seconds, TE=[15 . . . 90] ms; number-of-echo-times=6, echo-train-length=1, spatial-resolution=1.7× 1.7×3 mm$^3$, slice-thickness=3 mm, T$_{acquisition}$=22:00 minutes. Parameters for FIG. 5(b) are as follows: TR=2 seconds, TE=[10 . . . 220] ms, number-of-echo-times=22, echo-train-length=22, spatial-resolution=1.1×1.1×3 mm$^3$, slice-thickness=3 mm, T$_{acquisition}$=3:10 minutes. Parameters for FIG. 5(c) are as follows: TR=2 seconds, TE=[12 . . . 240] ms, number-of-echo-times=20, echo-train-length=20, spatial-resolution=1.7×1.7×3 mm$^3$, slice-thickness=3 mm, T$_{acquisition}$=3:10 minutes.

Figure 6:
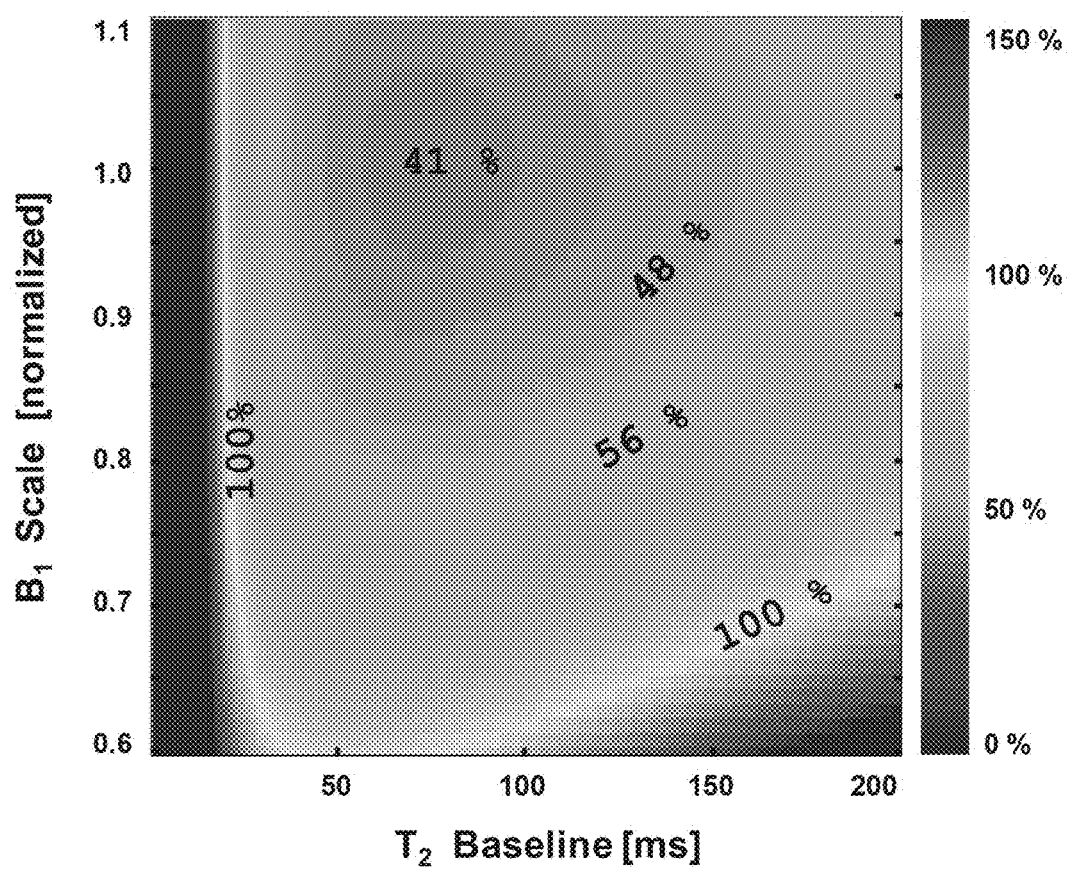
FIG. 6 illustrates the error in $T_2$ values for a conventional exponential fit of data generated by an MSE sequence.

Fitting MSE data to the conventional exponential model following Eq. 1 produces distorted T$_2$ values. Such distortion depends on factors including the T$_2$ baseline value, the slice profile or thickness, the number of echoes or the ETL, and refocusing of the pulse angle for the B$_1$ scale. The distortion may be spatially-dependent distortion that is sensitive to B$_1$ and B$_0$ field inhomogeneities. Such distortion is dependent on the protocol being used. Bloch simulations in some embodiments can predict the effects of stimulated echoes in multi-echo protocols with substantially higher accuracy than conventional exponential models. In some embodiments, an improvement in accuracy can be quantified. FIG. 6 illustrates the errors in T$_2$ values for an exponential fit of data generated by an MSE sequence, where the errors may be attributable to the aforementioned problems of fast sequences. Some embodiments of the present invention may effectively vitiate such errors.

At least some embodiments employ the simulation techniques described above in pre-processing a range of T$_2$ values. The pre-processing of the range of T$_2$ values allows for creation of a database of echo-modulation curves. Each of the curves corresponds to a unique T$_2$ value. The experimentally acquired data can then be matched pixel-by-pixel against the database using a best-fit criterion to determine the true T$_2$ values of the samples. The simulation techniques can be validated using reference single SE measurements. Such validation can be carried out using phantoms and in vivo so as to confirm the accuracy and robustness of the modeling techniques across a range of clinical settings.

In some embodiments, simulations of pulse sequences can be carried out to model the magnetization evolution during multi-echo acquisition. In some embodiments, one-dimensional imaging simulations can be carried out solely along the slice dimension. Both stimulated and indirect echoes are attributable to imperfect refocusing pulses encoding solely along the slice dimension. Furthermore, the flip angle variation along the slice profile can only be accounted for by simulating along the slice dimension. Thus, such embodiments permit high sampling resolution of ca. 2000 to 5000 spatial points, offering accurate tracking of all the coherence pathways for spin packets residing at each and every point along the slice profile. The simulated object can have, for example, a Gaussian spin density distribution (full width at half height=2.5 cm) and be positioned at the center of a 4 cm FOV and imaged with 4 mm spatial resolution. The simulation's internal resolution can be set to 140 μm in order to account for intra pixel dephasing effects, while the temporal resolution can be matched to be equivalent to the resolution for actual experiments.

In some embodiments, each run of the simulation generates a single echo-modulation curve, reflecting the intensity of each echo along the train for a given set of parameters. A database of simulated echo-modulation-curves ("EMCs") can be created by repeating the simulation for a range of T$_2$ values ([1 . . . 299] ms in steps of 1 ms and [300 . . . 1000] in steps of 5 ms) and transmit field (B1+) inhomogeneity scales ranging between 60% and 120%, where a value of 100% corresponds to a purely homogeneous B1+ field. The calculation time, in some embodiments, can be determined based on the number of simulated values of the T$_2$ and B1+ parameters and may range between 1 hour for a limited number of a priori known T$_2$ values to 10 hours for full high-resolution simulation of 60 B1+ inhomogeneity scales, 450 T$_2$ values, and ETL=10.

In some embodiments, a pronounced effect of stimulated echoes can be seen such that a second echo intensity may be higher than a first echo intensity, except for very short T$_2$ values, where a strong signal decay may dominate over the stimulated echo effect. The cumulative effect of higher order stimulated echoes may also be observed and may manifest as an even/odd modulation of later echoes. In some embodiments, the database of EMCs corresponding to different [T$_2$, B1+] pairs can include EMCs that may intersect one another. Nevertheless, such embodiments allow for the parameter selection process to identify a unique solution during post-processing. In some embodiments, uniqueness may depend on the experimental echo-train length (ETL), where too low ETL values may reduce the robustness of the parameter selection procedure.

In some embodiments, a method of mapping involves first generating T$_2$ maps from single SE data by fitting each pixel in the corresponding time-series of images to an exponential decay. Although the resulting maps may be affected by residual diffusion effects, these may be negligible in some embodiments in comparison to the variability of the T$_2$ values in vivo. Thus, the maps can serve a baseline reference for multi SE maps. Second, T$_2$ maps are generated from the multi SE data, first using the same exponential fit used for the single SE data, and then by matching to the pre-calculated database of simulated EMCs.

The EMC matching can be carried out for each pixel by calculating the L$_2$ norm of the difference between the experimental and simulated EMCs, and choosing the EMC giving the minimal value of the L$_2$-norm. In some embodiments, choosing the EMC involves searching over the entire database of simulated EMCs, which, due to the limited number of fit parameters, may be sufficiently fast so as to be completed in less than 1 minute per slice. The method further includes, following the matching, assigning a unique pair of [T$_2$, B1+] values to each pixel, yielding a pair of T$_2$ and B1+ parametric maps of the subject. In some embodiments, the method further includes evaluating the sensitivity of the algorithms used in the above-mentioned matching process to noise.

In some embodiments, the method further includes correcting distorted experimental data based on pre-calculated simulation values. Although T$_2$ maps reconstructed using the EMC algorithms of some embodiments exhibit high accuracy with respect to reference values, a measurement bias may be present. The measurement bias may be dependent on the underlying T$_2$ baseline value. Even the corrected T$_2$ values may not wholly reflect the actual physical spin-spin relaxation times of the tissue. Rather, the corrected T$_2$ values may be a spatiotemporal average over multiple mesoscopic domains residing within each macroscopic voxel.

In some embodiments, the database of simulated EMCs can be expanded to accommodate additional parameters and can allow for reconstruction of multiple contrasts from a single acquisition, as opposed to acquiring each contrast during a separate scan. Further, in some embodiments, the proton density can be modeled, and the EMC matching process can involve fitting multiple T$_2$ elements. In some embodiments, the EMC matching process is extended from a single T$_2$ to a multi-T$_2$ fitting according to Equation 2:

$$EMC^{experimental} = \sum_i a_i \cdot \left(EMC_{T_2^i}^{simulated}\right) \text{ s.t. } \sum a_i = 1 \quad \text{(Eq. 2)}$$

In some embodiments, the EMC matching process may be carried out on high performance computing systems. In other embodiments, a manual search of a limited subset or an entirety of the database of EMCs may be carried out. The matching process may be tailored in accordance with computational time constraints and resources. The present invention improves the accuracy for fast $T_2$ mapping, avoids the common disadvantages associated with the use of multi-echo sequences, and achieves significant error reduction. The present invention allows for a predetermined threshold within which error is maintained. Minimization or elimination of error may be desirable but difficult to realize, particularly in settings where a plurality of sources of error exist. Reducing the error norm so as not to exceed a predetermined threshold value can help to achieve heightened accuracy in generating each $T_2$ map.

Significantly improved fitting accuracy is achieved by modulating the effects of stimulated and indirect echoes. Such increased accuracy allows for generation of $T_2$ maps with high correlations to those acquired using single-echo SE sequences, which cannot be used in routine patients due to their long scan durations.

Methods of some embodiments of the present invention can improve quantification of parameters other than the $T_2$ relaxation time. Such parameters can be subject parameters representing phenomena of interest. To quantify a subject parameter, the method of at least one embodiment employs fitting based on an experimental set of echo modulation curves and a simulated set of echo modulation curves. In some embodiments, a Bloch simulation produces the simulated set of echo modulation curves based on at least one of a plurality of test parameters. For example, such test parameters may include an exact RF pulse shape based on amplitude and phase, an ETL value, a spatial distribution of a $B_1$ transmit field, a spatial distribution of a main $B_0$ magnetic field, a spatial distribution of $T_1$ relaxation time, a spatial distribution of a diffusion coefficient, slice thickness, acquisition bandwidth, and magnetic field gradient events applied during a pulse sequence.

In at least one embodiment relating to quantification of a subject parameter that is not a $T_2$ parameter, at least one run of a simulation is performed according to a protocol using at least one of the plurality of test parameters. The at least one run of the simulation is repeated for a plurality of values for the subject parameter. In the method of at least one embodiment, data is interpolated from the at least one run of the simulation to enhance resolution of the plurality of values for the subject parameter. Protocol data is acquired and a fitting procedure is performed. The method of some embodiments generates at least one map of values for the subject parameter.

The present invention achieves reliable $T_2$ mapping in clinically feasible scan times—as opposed to the prolonged, inconvenient, and mostly impractical times presently required—and with significantly reduced motion sensitivity compared to SE-based approaches. The reduction in scan times realizable by the present invention can be quantifiable, e.g., sampling ten points along a $T_2$ decay curve to acquire 10 echo times using an ETL=10 with an MSE sequence would correspond to a tenfold reduction in time in comparison to using an SE sequence, irrespective of spatial resolution. Embodiments of the present invention offer methods that are time efficient and use no a priori assumptions. Moreover, such methods provide comprehensive and easy-to-use frameworks that can be further used for modeling various acquisition schemes and a plurality of spin interactions including diffusion effects, weighted $T_2$ ("$T_2$*") relaxation and magnetic field non-uniformities.

In some embodiments, the reliability and stability of $T_2$ mapping can allow for improved investigation of diseases in areas where fast and accurate quantitative assessment of the $T_2$ relaxation time is essential but impractical in clinical routines. Common examples are neurodegenerative diseases that are associated with demyelination. In such cases, potential biomarkers such as a myelin-water fraction and an extra/intra-cellular water fraction are calculated based on numeric classification of the tissue $T_2$.

Embodiments of the invention permit quantitative mapping of $T_2$ relaxation times in vivo. Embodiments of the invention in clinical applications facilitate more accurate characterization of prostate and hepatic cancer, diagnosis of multiple sclerosis, musculoskeletal MRIs, characterization of brain lesions and other soft-tissue lesions, diagnosis of Parkinson's disease, characterization of atherosclerotic plaques, characterization of muscle physiology, and monitoring and follow-ups of cardiac transplant patients. Some embodiments of the invention in other clinical applications achieve greater accuracy in therapy decision-making for patients with acute stroke and improved therapy monitoring.

By way of illustration, the aforementioned techniques may be used to perform accurate $T_2$ mapping at 3T for cartilage assessment in patients with femoroacetabular impingement (FAI), as described below with reference to experimental results. The results were preliminarily validated against intra-operative findings.

A retrospective analysis was performed of 85 hips in 79 patients, 21 of whom underwent hip surgery following a diagnosis of FAI. The analysis was performed to investigate the utility of the quantitative $T_2$ relaxation time obtained as described above for detecting hip cartilage lesions in these patients. Quantitative $T_2$ maps were reconstructed from data acquired on four different 3T scanners using rapid MSE protocols. Three regions of interest (ROI) were defined, including one of both femoral and acetabular cartilage (ROI1), one covering just the central portion of the femoral cartilage (ROI2), and one containing only the weight-bearing portion of the acetabular cartilage (ROI3). The ability to detect arthroscopically confirmed cartilage lesions was evaluated for the mean, standard deviation and coefficient of variation in each ROI, as well as for a normalized $T_2$ index (defined as the ratio between the mean $T_2$ in ROI2 and ROI3).

As shown in FIGS. 5(a)-(c), spreads of $T_2$ indices per patient in the lesion and non-lesion groups were plotted. FIG. 5(a) depicts a spread of $T_2$ indices based on EMC fitting. FIG. 5(b) depicts a spread of $T_2$ indices using exponential fitting. FIG. 5(c) depicts a boxplot summary of the distributions in FIGS. 5(a) and 5(b). Results confirmed a statistically significant separation of patients with and without lesions using the mean $T_2$ value within ROI3 (p-value=0.053) and using the $T_2$ index (p-value<0.001). The $T_2$ index offered lesion detection with 100% specificity, 92.3% sensitivity and 95.2% accuracy. Thus, the techniques described herein were observed to yield accurate $T_2$ values that are consistent among scanners, and are independent of protocol implementation and parameter set. The quantitative $T_2$ index provides an objective measure of articular cartilage status and may improve preoperative assessments of FAI patients.

The ability of radiologic interpretation to assess cartilage status was also investigated by comparing the preoperative radiologic reports to surgical reports. Lower specificity, sensitivity and overall accuracy were found using morphologic evaluation yielding 38%, 69% and 57% respectively.

Figure 7:
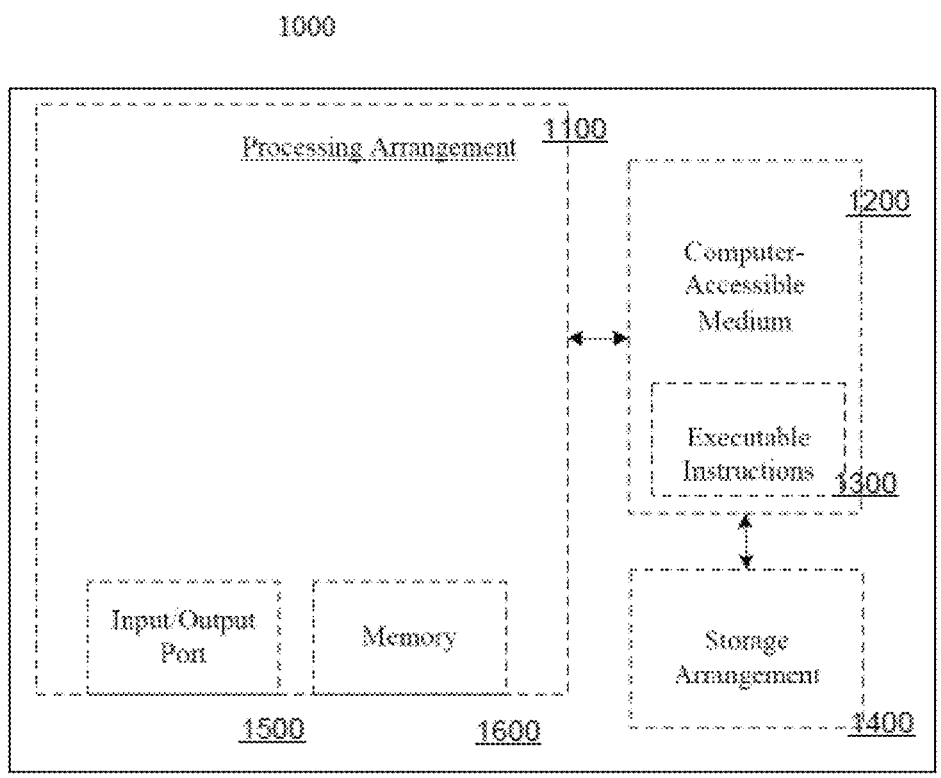
FIG. 7 illustrates a computer system for use with certain implementations.
Figure 8C:
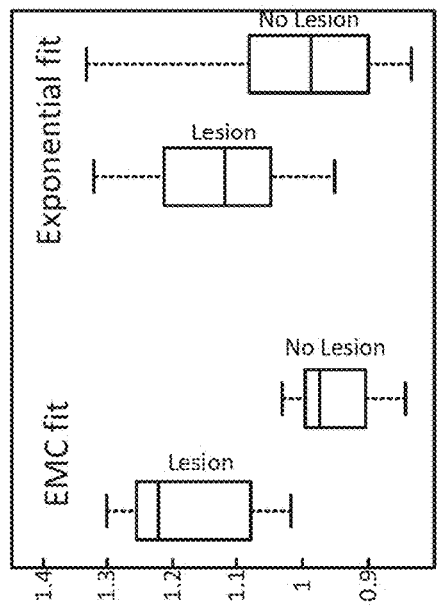
FIGS. 8(a)-(c) illustrate experimental results for $T_2$ indices.
Figure 8B:
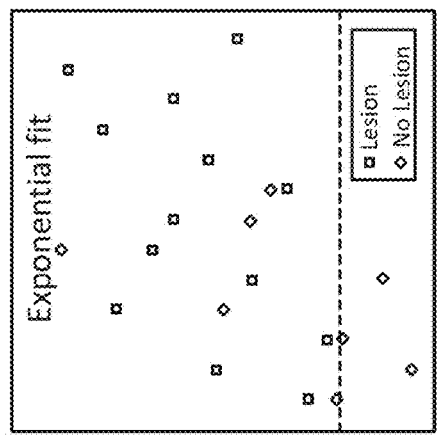
Figure 8A:
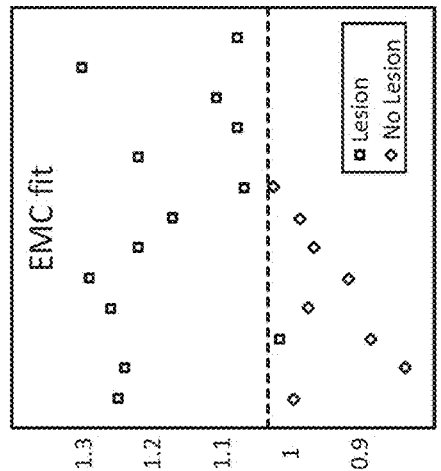

As shown in FIG. 7, e.g., a computer-accessible medium 1200 (e.g., as described herein, a storage device such as a hard disk, floppy disk, memory stick, CD-ROM, RAM, ROM, etc., or a collection thereof) can be provided (e.g., in communication with the processing arrangement 1100). The computer-accessible medium 1200 may be a non-transitory computer-accessible medium. The computer-accessible medium 1200 can contain executable instructions 1300 thereon. In addition or alternatively, a storage arrangement 1400 can be provided separately from the computer-accessible medium 1200, which can provide the instructions to the processing arrangement 1100 so as to configure the processing arrangement to execute certain exemplary procedures, processes and methods, as described herein, for example.

System 1000 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in a particular order, this should not be understood as requiring that such operations be performed in the particular order shown or in sequential order, or that all operations be performed, to achieve desirable results. Moreover, the separation of various aspects of the implementations described above should not be understood as requiring such separation in all implementations, and it should be understood that the described methods can generally be integrated in a single application or integrated across multiple applications.

Thus, particular implementations of the invention have been described. Other implementations are within the scope of the following claims. In some cases, actions recited in the claims may be performed in a different order and still achieve desirable results. In addition, the depictions in the accompanying figures do not necessarily require a particular order or sequential order.

What is claimed is:

1. A method for quantification of a spin-spin relaxation time ($T_2$) comprising:
    performing at least one run of a simulation of a prospective fast multi spin-echo (MSE) pulse sequence using at least one of a plurality of parameters;
    repeating the at least one run of the simulation for a plurality of $T_2$ values;
    producing a first set of echo modulation curves from the simulation, each of the curves being associated with a unique $T_2$ value of the plurality of $T_2$ values;
    acquiring MSE data from a scanner;
    deriving a second set of echo modulation curves from the acquired MSE data;
    fitting MSE data based on the first set of echo modulation curves and the second set of echo modulation curves; and
    generating at least one $T_2$ map from the fitted data,
    wherein fitting MSE data comprises using a piecewise linear correlation between the first set of echo modulation curves and the second set of echo modulation curves, and
    wherein the correlation exceeds a predetermined threshold.

2. The method of claim 1, further comprising interpolating data from the at least one run of the simulation to enhance resolution of the plurality of $T_2$ values.

3. The method of claim 1, wherein the at least one run of the simulation is repeated in a plurality of increments; and wherein the plurality of $T_2$ values correspond to an expected range of $T_2$ values.

4. The method of claim 1, wherein fitting MSE data comprises reducing an error norm based on comparison of the first set of echo modulation curves and the second set of echo modulation curves, and
wherein the error norm is reduced in accordance with a predetermined threshold that the error norm does not exceed.

5. The method of claim 1, further comprising reducing an error norm using an iterative least-square optimization approach.

6. The method of claim 1, further comprising reducing an error norm based on both the first set and the second set of echo modulation curves.

7. The method of claim 1, wherein MSE data is acquired from a specimen disposed in the scanner.

8. The method of claim 1, wherein one of the plurality of parameters is an experimental parameter.

9. The method of claim 1, wherein one of the plurality of parameters is a radio-frequency pulse amplitude.

10. The method of claim 1, wherein one of the plurality of parameters is a frequency off-resonance of a main $B_0$ magnetic field.

11. The method of claim 1, wherein one of the plurality of parameters is a T1 relaxation time.

12. The method of claim 1, wherein one of the plurality of parameters is a diffusion coefficient.

13. The method of claim 1, wherein one of the plurality of parameters is a slice-thickness.

14. The method of claim 1, wherein one of the plurality of parameters is an acquisition bandwidth or an acquisition duration.

15. The method of claim 1, wherein one of the plurality of parameters is an echo train length.

16. The method of claim 1, wherein one of the plurality of parameters is an exact radio-frequency pulse shape.

17. A device for diagnosis patients according to the method of claim 1.

18. A device for quantifying a spin-spin relaxation time ($T_2$) comprising:
a control unit comprising a processor and a memory, and configured to generate at least one run of a simulation of a prospective fast multi spin-echo (MSE) pulse sequence using at least one of a plurality of parameters to produce a first set of echo modulation curves; and
a magnetic resonance data acquisition unit coupled to the control unit, the control unit being configured to analyze MSE data elicited from the magnetic resonance data acquisition unit,
wherein the control unit is configured to analyze MSE data elicited from the magnetic resonance data acquisition unit to generate a second set of echo modulation curves to permit comparison to the first set of echo modulation curves,
wherein the control unit is configured to fit the MSE data using a piecewise linear correlation between the first set of echo modulation curves and the second set of echo modulation curves, and
wherein the correlation exceeds a predetermined threshold.

19. A method for quantification of a subject parameter comprising:
performing at least one run of a simulation according to a protocol using at least one of a plurality of test parameters;
repeating the at least one run of the simulation for a plurality of values for the subject parameter;
producing a first set of echo modulation curves from the simulation, each of the curves being associated with a unique value of the plurality of values for the subject parameter;
acquiring fast multi spin-echo protocol data;
deriving a second set of echo modulation curves from the acquired MSE protocol data;
fitting MSE protocol data based on the first set of echo modulation curves and the second set of echo modulation curves; and
generating at least one map of values for the subject parameter from the fitted data,
wherein fitting MSE data comprises using a piecewise linear correlation between the first set of echo modulation curves and the second set of echo modulation curves, and
wherein the correlation exceeds a predetermined threshold.

20. The method of claim 19, further comprising interpolating data from the at least one run of the simulation to enhance resolution of the plurality of values for the subject parameter.

21. A method for quantification of a spin-spin relaxation time ($T_2$) comprising:
receiving, from a simulation, a first set of echo modulation curves, each of the curves being associated with a unique $T_2$ value of a plurality of $T_2$ values for a prospective fast multi spin-echo (MSE) pulse sequence;
receiving MSE data from a scanner;
receiving a second set of echo modulation curves derived from the MSE data received from the scanner;
fitting MSE data based on the first set of echo modulation curves and the second set of echo modulation curves; and
generating at least one $T_2$ map from the fitted data,
wherein fitting MSE data comprises using a piecewise linear correlation between the first set of echo modulation curves and the second set of echo modulation curves, and
wherein the correlation exceeds a predetermined threshold.

22. The method of claim 21, further comprising interpolating data from the received set of curves to enhance resolution of the plurality of $T_2$ values.

23. A non-transitory computer-readable storage medium for a computer system including a processor, the computer-readable storage medium having instructions stored thereon that, when executed by the processor, cause the computer system to perform operations comprising:
receiving, from a simulation, a first set of echo modulation curves, each of the curves being associated with a unique $T_2$ value of a plurality of $T_2$ values for a prospective fast multi spin echo (MSE) pulse sequence;
receiving MSE data from a scanner;
receiving a second set of echo modulation curves derived from the MSE data received from the scanner;
fitting MSE data based on the first set of echo modulation curves and the second set of echo modulation curves; and
generating at least one $T_2$ map from the fitted data,
wherein fitting MSE data comprises using a piecewise linear correlation between the first set of echo modulation curves and the second set of echo modulation curves, and wherein the correlation exceeds a predetermined threshold.

24. The non-transitory computer-readable storage medium of claim 23, wherein the computer system is configured to perform further operations comprising:
creating a database from the received set of curves, and interpolating data from the received set of curves to enhance resolution of the plurality of $T_2$ values.

* * * * *